US006149580A

United States Patent [19]

Dabney

[11] Patent Number: 6,149,580

[45] Date of Patent: Nov. 21, 2000

[54] MEDICAL DEVICE TO AID IN EJACULATION

[76] Inventor: J. Conway Dabney, 2125 Wrens Way, Clearwater, Fla. 33764

[21] Appl. No.: 09/238,532

[22] Filed: Jan. 27, 1999

[51] Int. Cl.[7] ........ A61F 5/00

[52] U.S. Cl. ........ 600/38; 600/39

[58] Field of Search ........ 600/38, 39

[56] References Cited

U.S. PATENT DOCUMENTS

| | | | |
|---|---|---|---|
| 1,383,944 | 7/1921 | Hart | 600/39 |
| 5,695,446 | 12/1997 | Lindholm-Ventola | 600/38 |
| 5,782,818 | 7/1998 | Shubin | 600/38 |
| 5,876,324 | 3/1999 | Trouchine | 600/38 |

*Primary Examiner*—Max Hindenburg
*Assistant Examiner*—Brian Szmal

[57] ABSTRACT

A medical device to aid in masturbation including a core member formed in a cylindrical configuration. The core member has an interior surface and an exterior surface with a first end and an axially spaced second end. A surrounding member is formed in a cylindrical configuration and has an interior and exterior surfaces with a first end and an axially spaced second end. The surrounding member has a central section is positioned within the core member and end regions stretched to be in contact with the exterior surface of the core member adjacent to the ends to thereby form a central cylindrical section and adjacent frustoconical sections.

13 Claims, 4 Drawing Sheets

FIG 1
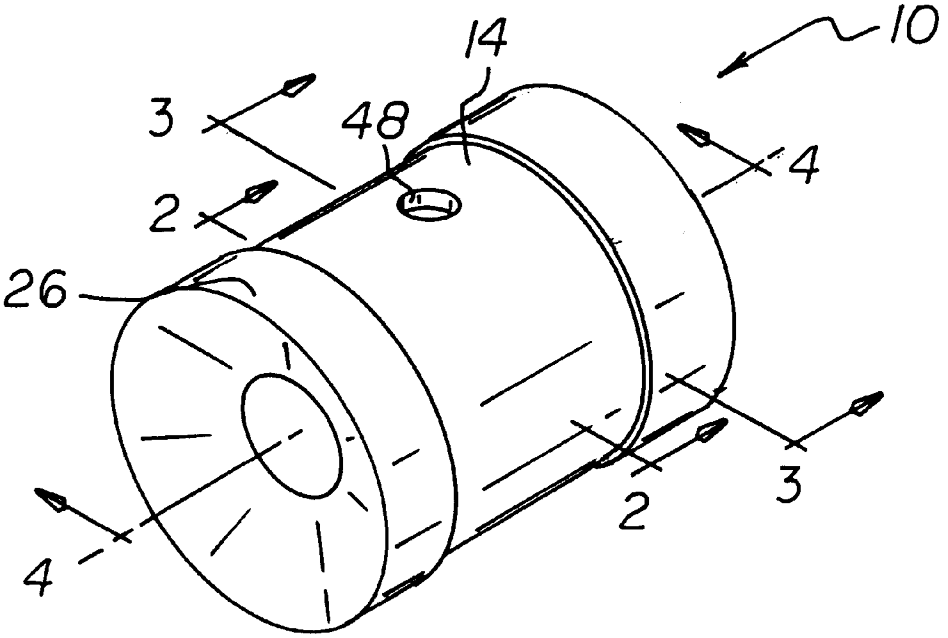
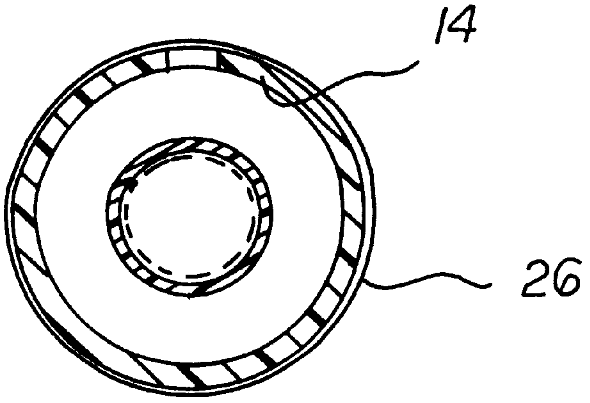
FIG 2

MEDICAL DEVICE TO AID IN EJACULATION

BACKGROUND OF THE INVENTION

1. Field of the Invention

The present invention relates to a medical device to aid in masturbation and more particularly pertains to assisting in the ejaculation of sperm through the use of a masturbation aid.

2. Description of the Prior Art

The use of medical aids for sex purposes of known designs and configurations is known in the prior art. More specifically, medical aids for sex purposes of known designs and configurations heretofore devised and utilized for the purpose of assisting in masturbation through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,501,650 to Reinhard R. Gellert discloses an automated masturbatory device. While this device and other known devices fulfill their respective, particular objectives and requirements, the aforementioned patents do not describe a medical device to aid in masturbation that allows assisting in ejaculation of sperm through the use of a masturbation aid.

In this respect, the medical device to aid in masturbation according to the present invention substantially departs from the conventional concepts and designs of the prior art, and in doing so provides an apparatus primarily developed for the purpose of assisting in the ejaculation of sperm through the use of a masturbation aid.

Therefore, it can be appreciated that there exists a continuing need for a new and improved medical device to aid in masturbation which can be used for assisting in the ejaculation of sperm through the use of a masturbation aid. In this regard, the present invention substantially fulfills this need.

SUMMARY OF THE INVENTION

In view of the foregoing disadvantages inherent in the known types of medical aids for sex purposes of known designs and configurations now present in the prior art, the present invention provides an improved medical device to aid in masturbation. As such, the general purpose of the present invention, which will be described subsequently in greater detail, is to provide a new and improved medical device to aid in masturbation and method which has all the advantages of the prior art and none of the disadvantages.

To attain this, the present invention essentially comprises a core member. The core member is formed in a cylindrical configuration. The core member is fabricated of a generally rigid plastic material. The preferred material is polyvinylchloride. The core member has an interior surface and an exterior surface with a first end and an axially spaced second end. The core member has an axial length of between about 1½ inches and 2½ inches, preferably 2 inches. The core member has an inside diameter of between about 1½ inches and 2 inches, preferably 1¾ inches. The core member has an outside diameter of between about 1¾ inches and 2¼ inches, preferably 2 inches. The core member has a wall thickness of between about ⅙ inch and $\frac{3}{16}$ inch preferably ⅛ inch. Next provide is a surrounding member. The surrounding member is formed in a cylindrical configuration. The surrounding member is fabricated of a flexible, resilient, rubber-like material, natural or synthetic or blends thereof. The preferred material is latex. The surrounding member has an interior surface. The surrounding member also has an exterior surface. The surrounding member has a first end and an axially spaced second end. The surrounding member has an axial length of between about 4 inches and 5 inches, preferably 4½ inches. The surrounding member has an inside diameter of between about 1¼ inches and 1¾ inches, preferably 1½ inches. The surrounding member has an outside diameter of between about $1\frac{9}{32}$ inches and $1\frac{25}{32}$ inches, preferably $1\frac{17}{32}$ inches. The wall thickness of the surrounding member is between about $\frac{1}{64}$ inch and $\frac{3}{64}$ inch, preferably $\frac{1}{32}$ inch. The surrounding member has a central section positioned within the core member. End regions of the surrounding member are stretched into contact with the exterior surface of the core member adjacent to the ends to thereby form a central cylindrical section and adjacent frustoconical sections. Next provided is a lubricant covering the interior surface of the surrounding member within the core member. The preferred lubricant is a commercially available jelly such as K-Y Jelly. Other lubricants, such as Vaseline, could readily be utilized. A hole 48 is formed in the core member. The hole is located at about a midpoint along the axis of the core member. The hole extends radially through the core. The hole has a diameter of between about ⅛ inch and ⅜ inch, preferably ¼ inch. In this manner air is allowed to flow to and from the region between the interior surface of the core member and the interior surface of the surrounding member. Next provide is a valve. The valve is formed as a tube extending radially outwardly from the hole. A ball is pivotally mounted within the tube. The ball is mounted on pins. A hole is provided in the ball. Lastly, an adjacent handle functions to rotate the ball 90 degrees between an orientation where the axis of the hole in the ball is in alignment with the axis of the hole in the core member to allow the flow of air therethrough and a closed position wherein the hole has its axis perpendicular to the axis of the core member for precluding the flow of air therethrough.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved medical device to aid in masturbation which has all of the advantages of the prior art medical aids for sex purposes of known designs and configurations and none of the disadvantages.

It is another object of the present invention to provide a new and improved medical device to aid in masturbation which may be easily and efficiently manufactured and marketed.

It is further object of the present invention to provide a new and improved medical device to aid in masturbation which is of durable and reliable constructions.

An even further object of the present invention is to provide a new and improved medical device to aid in masturbation which is susceptible of a low cost of manufacture with regard to both materials and labor, and which accordingly is then susceptible of low prices of sale to the consuming public, thereby making such medical device to aid in masturbation economically available to the buying public.

Still another object of the present invention is to aid in ejaculation to collect semen.

Still another object of the present invention is to provide a vaginal substitute which is an absolute contraceptive.

Still another object of the present invention is to provide a vaginal substitute which can be an aid in prevention of the spread of AIDS and other sexually transmitted diseases.

Still another object of the present invention is to provide a vaginal substitute in the case of painful female pelvic disorders or times of the month when sexual activity would normally be avoided.

Even still another object of the present invention is to provide a medical device to aid in masturbation for assisting in the ejaculation of sperm through the use of a masturbation aid.

Lastly, it is an object of the present invention to provide a new and improved medical device to aid in masturbation including a core member formed in a cylindrical configuration and having an interior surface and an exterior surface with a first end and an axially spaced second end, and a surrounding member formed in a cylindrical configuration and having interior and exterior surfaces with a first end and an axially spaced second end and a central section positioned within the core member and end regions stretched to be in contact with the exterior surface of the core member adjacent to the ends to thereby form a central cylindrical section and adjacent frustoconical sections.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the new and improved medical device to aid in ejaculation constructed in accordance with the principles of the present invention.

FIG. 2 is a cross-sectional view taken transverse to the axis to the central extent thereof.

The same reference numerals refer to the same parts throughout the various Figures.

DESCRIPTION OF THE PREFERRED EMBODIMENT

Figure 3:
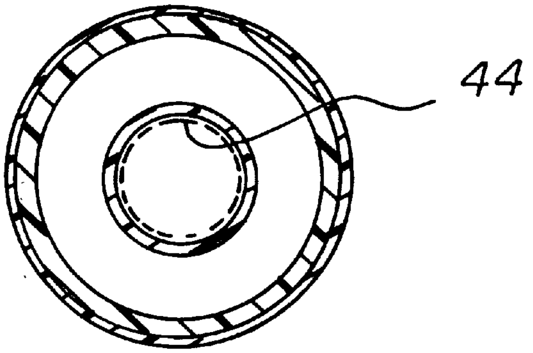
FIG. 3 is a cross-sectional view of the device taken transverse to the axis adjacent to one end thereof.
Figure 5:
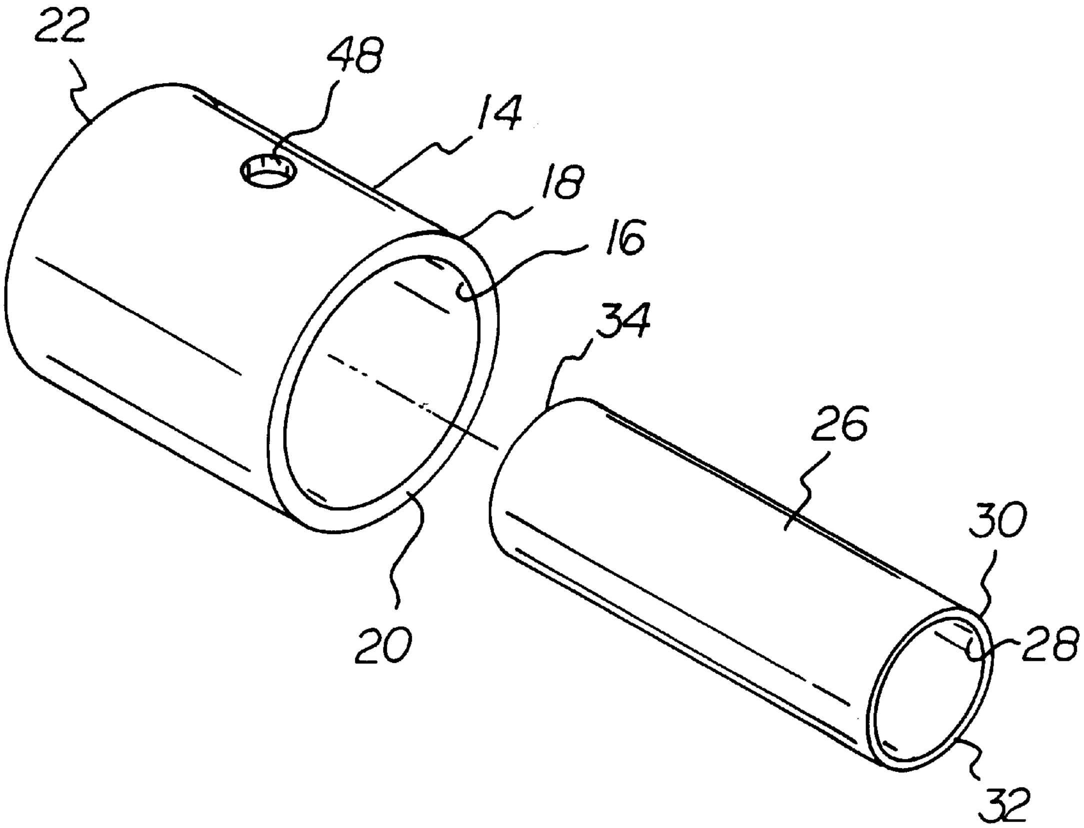
FIG. 5 is an exploded perspective view of the system as shown in the prior figures.
Figure 4:
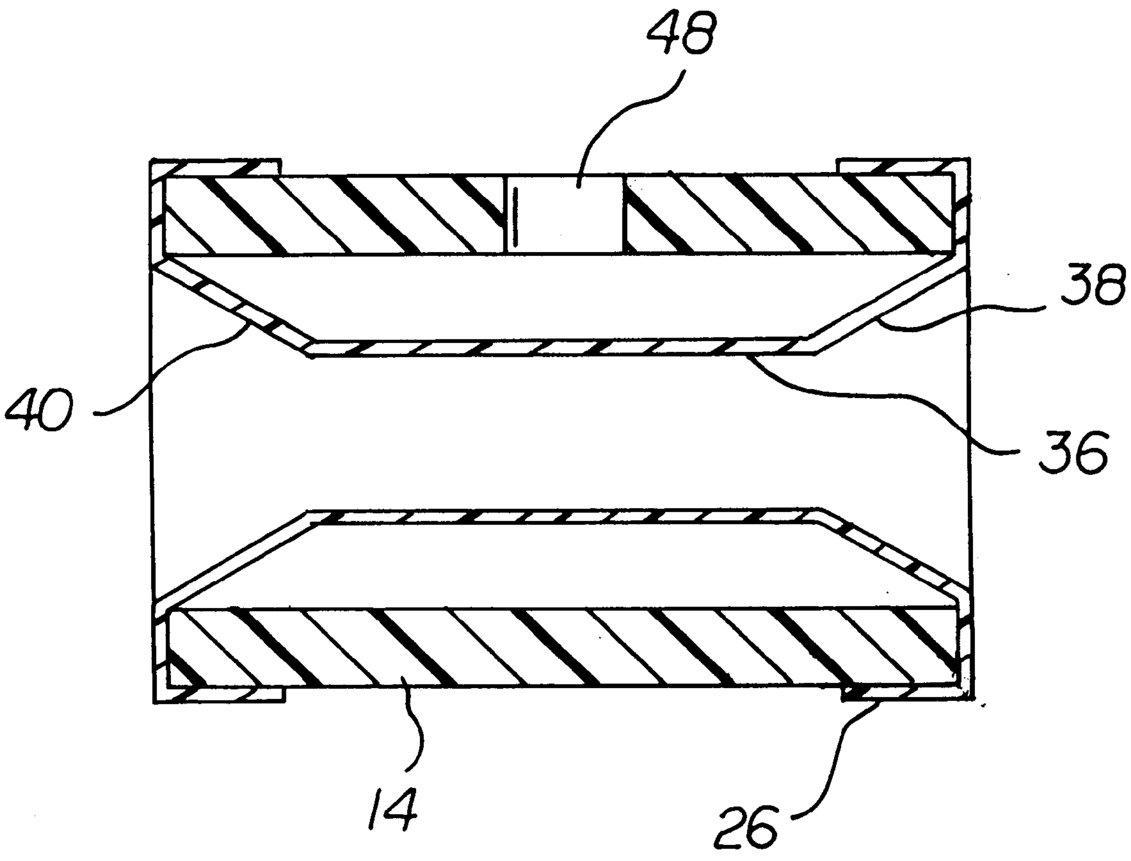
FIG. 4 is a cross-sectional view taken along the axis thereof.
Figure 6:
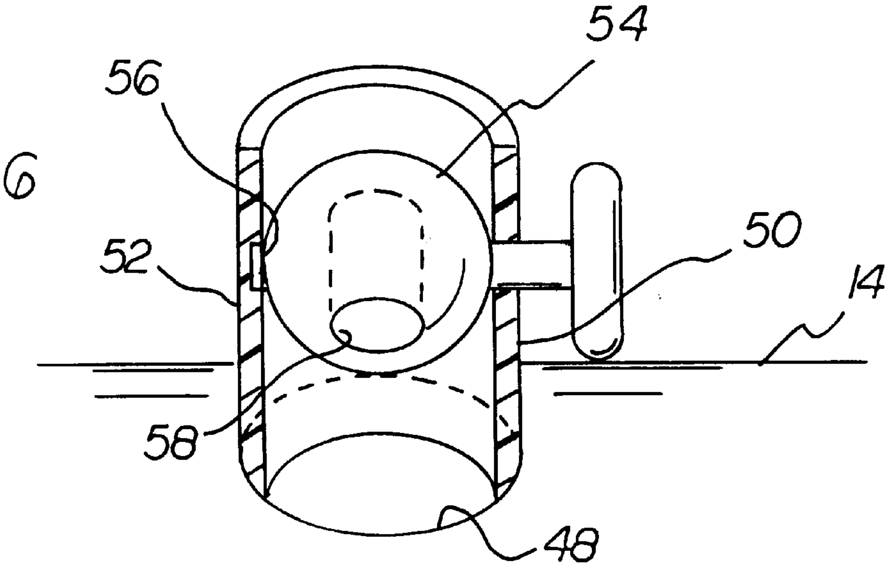
FIG. 6 is a perspective view of the core member employing a valve in accordance with an alternate embodiment of the invention.
Figure 7:
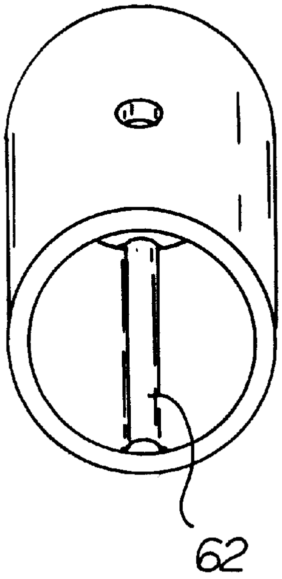
FIG. 7 is a perspective view of the core member formed with a linear axis projection.
Figure 8:
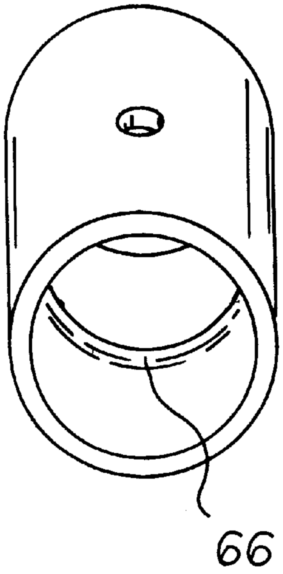
FIG. 8 is a perspective view of the core member formed with an annular ridge.
Figure 9:
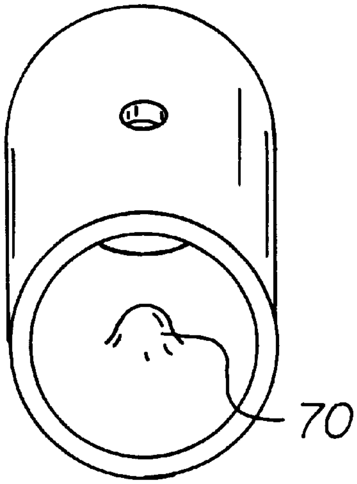
FIG. 9 is a perspective view of the core member formed with an interior hemispherical enlargement.

With reference now to the drawings, and in particular to FIG. 1 thereof, the preferred embodiment of the new and improved medical device to aid in masturbation embodying the principles and concepts of the present invention and generally designated by the reference numeral 10 will be described.

The present invention, the medical device to aid in ejaculation 10 is comprised of a plurality of components. Such components in their broadest context include a core member and a surrounding member. Such components are individually configured and correlated with respect to each other so as to attain the desired objective.

A core member 14 is formed in a cylindrical configuration. The core member is fabricated of a generally rigid plastic material. The preferred material is polyvinylchloride. The core member has an interior surface 16 and an exterior surface 18 with a first end 20 and an axially spaced second end 22. The core member has an axial length of between about 1½ inches and 2½ inches, preferably 2 inches. The core member has an inside diameter of between about 1½ inches and 2 inches, preferably 1¾ inches. The core member has an outside diameter of between about 1¾ inches and 2¼ inches, preferably 2 inches. The core member has a wall thickness of between about ⅙ inch and 3/16 inch preferably ⅛ inch.

Next provided is a surrounding member 26. The surrounding member is formed in a cylindrical configuration. The surrounding member is fabricated of a flexible, resilient, rubber-like material, natural or synthetic or blends thereof. The preferred material is latex. The surrounding member has an interior surface 28. The surrounding member also has an exterior surface 30. The surrounding member has a first end 32 and an axially spaced second end 34. The surrounding member has an axial length of between about 4 inches and 5 inches, preferably 4½ inches. The surrounding member has an inside diameter of between about 1¼ inches and 1¾ inches, preferably 1½ inches. The surrounding member has an outside diameter of between about 1 9/32 inches and 1 25/32 inches, preferably 1 17/32 inches. The wall thickness of the surrounding member is between about 1/64 inch and 3/64 inch, preferably 1/32 inch. The surrounding member has a central section 36 positioned within the core member. End regions 38 and 40 of the surrounding member are stretched into contact with the exterior surface of the core member adjacent to the ends to thereby form a central cylindrical section and adjacent frustoconical sections.

Next provided is a lubricant 44 covering the interior surface of the surrounding member within the core member. The preferred lubricant is a commercially available jelly such as K-Y Jelly™. Other lubricants, such as Vaseline™, could readily be utilized.

A hole 48 is formed in the core member. The hole is located at about a mid point along the axis of the core member. The hole extends radially through the core. The hole has a diameter of between about ⅛ inch and ⅜ inch, preferably ¼ inch. In this manner air is allowed to flow to and from the region between the interior surface of the core member and the interior surface of the surrounding member.

Next provided is a valve 50. The valve is formed as a tube 52 extending radially outwardly from the hole. A ball 54 is pivotally mounted within the tube. The ball is mounted on pins 56. A hole 58 is provided in the ball. An adjacent handle functions to rotate the ball 90 degrees between an orientation where the axis of the hole in the ball is in alignment with the axis of the hole in the core member to allow the flow of air therethrough and a closed position wherein the hole has its axis perpendicular to the axis of the core member for precluding the flow of air therethrough.

In an alternate embodiment, an axial protrusion 62 is provided on the interior surface of the core member. In still another alternate embodiment, an annular ridge 66 is provided on the interior surface of the core member. And in still another alternate embodiment, a generally hemispherical enlargement 70 is provided. The hemispherical enlargement extends radially inwardly from the interior surface of the core member.

The device as described herein above is of a length to be located and axially reciprocated on the shaft of the user's penis, remote from the scrotum and remote from the head and the sensitive area between the head and the shaft. The diameter is such as to provide contact with the resilient surrounding member normally backed by the cushioning air space. This arrangement provides for the greatest comfort, efficiency and simulation of intercourse. In this manner, the device as described herein above functions.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A medical device to aid in ejaculation, comprising in combination:

a core member formed in a cylindrical configuration, the core member being fabricated of a generally rigid plastic material, preferably polyvinylchloride, the core member having an interior surface and an exterior surface with a first end and an axially spaced second end, the core member having an axial length of between about 1½ inches and 2½ inches, preferably 2 inches, and an inside diameter of between about 1½ inches and 2 inches, preferably 1¾ inches, and an outside diameter of between about 1¾ inches and 2¼ inches, preferably 2 inches, and a wall thickness of between about ⅙ inch and 3/16 inch preferably ⅛ inch;

a surrounding member formed in a cylindrical configuration, the surrounding member being fabricated of a flexible, resilient, rubber-like material, natural or synthetic or blends thereof, preferably latex, the surrounding member having an interior surface and an exterior surface with a first end and an axially spaced second end, the surrounding member having an axial length of between about 4 inches and 5 inches, preferably 4½ inches, and an inside diameter of between about 1¼ inches and 1¾ inches, preferably 1½ inches, and an outside diameter of between about 1 9/32 inches and 1 25/32 inches, preferably 1 17/32 inches, and a wall thickness of between about 1/64 inch and 3/64 inch preferably 1/32 inch, the surrounding member having a central section positioned within the core member and end regions stretched into contact with the exterior surface of the core member adjacent to the ends to thereby form a central cylindrical section and adjacent frustoconical sections, the core member and surrounding member forming there between a single uninterrupted annular chamber formed with a common diameter circular configuration radially over the majority of its extent and with a common trapezoidal configuration axially;

a lubricant covering the interior surface of the surrounding member within the core member;

a hole formed in the core member at about a mid point along the axis thereof and extending radially through the core, the hole having a diameter of between about ⅛ inch and ⅜ inch, preferably ¼ inch, for allowing the flow of air to and from the region between the interior surface of the core member and the interior surface of the surrounding member; and a valve formed as a tube extending radially outwardly from the hole with a ball pivotally mounted therein on pins, the ball having a hole therethrough with an adjacent handle to rotate the ball 90 degrees between an orientation where the axis of the hole in the ball is in alignment with the axis of the hole in the core member to allow the flow of air therethrough and a closed position wherein the hole has its axis perpendicular to the axis of the core member for precluding the flow of air therethrough.

2. A medical device to aid in masturbation, comprising:

a core member formed in a cylindrical configuration, the core member having an interior surface and an exterior surface with a first end and an axially spaced second end; and a surrounding member formed in a cylindrical configuration, the surrounding member having an interior surface and an exterior surface with a first end and an axially spaced second end, the surrounding member having a central section positioned within the core member and end regions stretched to be in contact with the exterior surface of the core member adjacent to the ends to thereby form a central cylindrical section and adjacent frustoconical sections, the core member and surrounding member forming there between a single uninterrupted annular chamber formed with a common diameter circular configuration radially over the majority of its extent and with a common trapezoidal configuration axially.

3. The device as set forth in claim 2 and further including a lubricant covering the interior surface of the surrounding member within the core member.

4. The device as set forth in claim 2 and further including a hole formed in the core member at about a mid point along the axis thereof and extending radially through the core for allowing the flow of air to and from the region between the interior surface of the core member and the exterior surface of the surrounding member.

5. The device as set forth in claim 4 and further including a valve formed as a tube extending radially outwardly from the hole with a ball pivotally mounted therein on pins, the ball having a hole therethrough with an adjacent handle to rotate the ball 90 degrees between an orientation where the axis of the hole in the ball is in alignment with the axis of the hole in the core member to allow the flow of air therethrough and a closed position wherein the hole has its axis perpendicular to the axis of the core member for precluding the flow of air therethrough.

6. The device as set forth in claim 2 wherein the core member is fabricated of a generally rigid plastic material, preferably polyvinylchloride.

7. The device as set forth in claim 2 wherein the core member has an axial length of between about 1½ inches and 2½ inches, preferably 2 inches, and an inside diameter of between about 1½ inches and 2 inches, preferably 1¾ inches, and an outside diameter of between about 1¾ inches and 2¼ inches, preferably 2 inches, and a wall thickness of between about ⅙ inch and 3/16 inch preferably ⅛ inch.

8. The device as set forth in claim 2 wherein the surrounding member is fabricated of a flexible, resilient, rubber-like material, natural of synthetic or blends thereof, preferably latex.

9. The device as set forth in claim 2 wherein the surrounding member has an interior surface and an exterior surface with a first end and an axially spaced second end, the core member having an axial length of between about 4 inches and 5 inches, preferably 4½ inches, and an inside diameter of between about 1¼ inches and 1¾ inches, preferably 1½ inches, and an outside diameter of between about 1 9/32 inches and 1 25/32 inches, preferably 1 17/32 inches, and a wall thickness of between about 1/64 inch and 3/64 inch preferably 1/32 inch, the surrounding member having a central section positioned within the core member and end regions stretched to be in contact with the exterior surface of the core member adjacent to the ends to thereby form a central cylindrical section and end frustoconical sections.

10. The device as set forth in claim 2 wherein the overall external diameter of the system is essentially equal to the overall axial length of the system, plus or minus 10 percent.

11. The device as set forth in claim 2 and further including an axial protrusion in the interior surface of the core member.

12. The device as set forth in claim 2 and further including an annular ridge on the interior surface of the core member.

13. The device as set forth in claim 2 and further including a generally hemispherical enlargement extending radially inwardly from the interior surface of the core member.

* * * * *